United States Patent
Sonehara et al.

(10) Patent No.: US 7,989,755 B2
(45) Date of Patent: Aug. 2, 2011

(54) APPARATUS FOR PHOTON DETECTION INCLUDING A SAMPLE CELL WITH AN OUTER SURFACE WITH A CURVED BOTTOM, AND A PINHOLE CREATED ON A PINHOLE PLATE

(75) Inventors: Tsuyoshi Sonehara, Kokubunji (JP); Takashi Anazawa, Koganei (JP)

(73) Assignee: Hitachi, Ltd., Tokyo (JP)

( * ) Notice: Subject to any disclaimer, the term of this patent is extended or adjusted under 35 U.S.C. 154(b) by 64 days.

(21) Appl. No.: 11/672,597

(22) Filed: Feb. 8, 2007

(65) Prior Publication Data

US 2007/0210269 A1    Sep. 13, 2007

(30) Foreign Application Priority Data

Mar. 13, 2006   (JP) .................................. 2006-067937

(51) Int. Cl.
*H01J 3/14* (2006.01)
*H01J 40/14* (2006.01)

(52) U.S. Cl. ........................................ 250/216; 250/239

(58) Field of Classification Search ............... 250/208.1, 250/221, 458.1–467.1, 239, 559.4, 216, 227.25; 359/368, 656, 641; 356/337, 338, 39, 244
See application file for complete search history.

(56) References Cited

U.S. PATENT DOCUMENTS

| | | | | |
|---|---|---|---|---|
| 5,576,827 A | * | 11/1996 | Strickland et al. | 356/336 |
| 6,120,734 A | * | 9/2000 | Lackie | 422/68.1 |
| 6,376,843 B1 | * | 4/2002 | Palo | 250/458.1 |
| 6,388,788 B1 | * | 5/2002 | Harris et al. | 359/196.1 |
| 6,741,347 B1 | * | 5/2004 | Scaiano et al. | 356/319 |
| 7,369,220 B2 | * | 5/2008 | Okazaki | 356/123 |
| 2002/0097489 A1 | * | 7/2002 | Kawano et al. | 359/388 |
| 2007/0008536 A1 | * | 1/2007 | Mitani et al. | 356/417 |

FOREIGN PATENT DOCUMENTS

| | | |
|---|---|---|
| JP | 04-369463 | 12/1992 |
| JP | 08-178831 | 7/1996 |
| JP | 09-043197 | 2/1997 |
| JP | 10-221242 | 8/1998 |
| JP | 11-173987 | 7/1999 |
| JP | 2000-097844 | 4/2000 |
| JP | 2002-502955 | 1/2002 |
| JP | 2003-004629 | 1/2003 |
| JP | 2003-508785 | 3/2003 |
| JP | 2004-085443 | 3/2004 |
| JP | 2004-138420 | 5/2004 |
| JP | 2004-340752 | 12/2004 |
| JP | 2005-227098 | 8/2005 |
| JP | 2005-535871 | 11/2005 |

* cited by examiner

*Primary Examiner* — Que T Le
*Assistant Examiner* — Pascal M Bui-Pho
(74) *Attorney, Agent, or Firm* — Antonelli, Terry, Stout & Kraus, LLP.

(57) ABSTRACT

The object of the present invention is to acquire the brightness of NA>1 while alleviating the requirement for the precision of positioning for the collection lens of the sample cell in a non-liquid immersion system. In order to achieve the object mentioned above, the bottom of the sample cell is formed in a curved surface, and an arrangement is made to ensure that the fluorescence irradiated from the focusing point would be parallel pencils when emitted by the cell, and in addition a pinhole is disposed at the focal point of the fluorescence collection lens.

17 Claims, 10 Drawing Sheets

PRIOR ART

PLAN VIEW OF THE SAMPLE CELL
CORRESPONDING WITH PLURAL SAMPLES

CROSS SECTION BY PLANE A

APPARATUS FOR PHOTON DETECTION INCLUDING A SAMPLE CELL WITH AN OUTER SURFACE WITH A CURVED BOTTOM, AND A PINHOLE CREATED ON A PINHOLE PLATE

CLAIM OF PRIORITY

The present application claims priority from Japanese application JP 2006-067937 filed on Mar. 13, 2006, the content of which is hereby incorporated by reference into this application.

FIELD OF THE INVENTION

The present invention relates to an apparatus for photon detection preferred in quantifying fluorescence-labeled biomolecules by irradiating sample solution containing the biomolecules with photon and by detecting the excited fluorescence.

BACKGROUND OF THE INVENTION

To quantify fluorescence-labeled biomolecules, an analysis apparatus for irradiating the sample solution with photon in such a way that photons may converge at a point (hereinafter referred to as "focusing point") within the solution to excite the fluorescence, collecting the fluorescence irradiated by the biomolecules in the solution and transmitting through the sample cell with the collection lens, and thus detecting only the photons forming image on a pinhole placed on the conjugate point of the focusing point and transmitting through the pinhole is generally used. By detecting only the photons transmitting through the pinhole, the volume for detecting the fluorescence in the sample (detection volume) is limited to the vicinity of the focusing point, and background light (B) such as luminescence of solution at anywhere other than the vicinity of the focusing point, scattering light at the surface of the sample cell is blocked, and thus it is possible to detect the fluorescence from biomolecules in the detection volume (signal, S) with a good signal to background (S/B) ratio.

Figure 1:
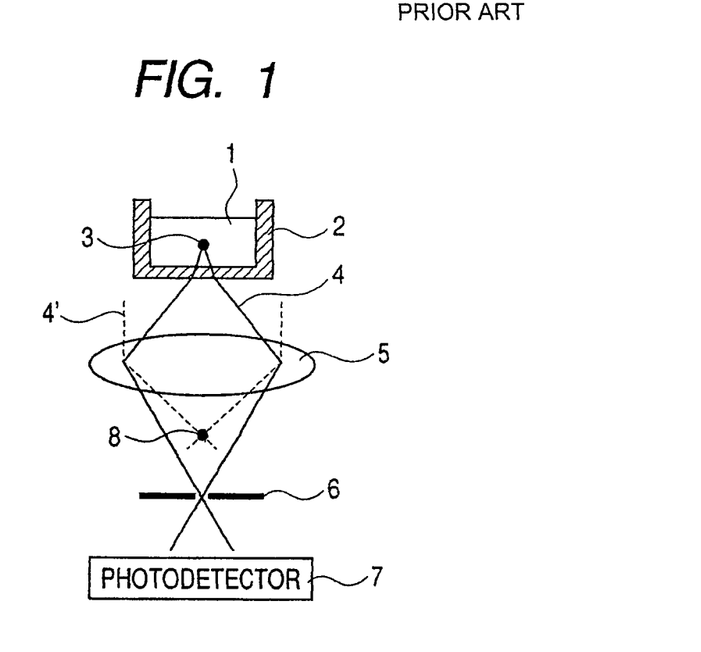
FIG. 1 is an illustration of the structure of a conventional fluorescence detection system having a pinhole.

The detection system of this type of apparatus is generally constituted as shown in FIG. 1. Excited beam is focused at the sample 1 in the sample cell 2, and the fluorescence 4 emitted from the focusing point 3 is collected at the pinhole on the pinhole plate 6 created at a conjugate position with the focusing point 3 by means of the collection lens 5, and is detected by the photodetector 7 passing through the pinhole. In reality, the lens 5 is a combination lens made of a plurality of lens, incorporating a filter, a dichroic mirror and the like between the lens. In FIG. 1 which is a schematic illustration showing the basic principle, however, we used a simplified structure for its illustration. As B is reduced to a sufficiently low level in a system like the one shown in FIG. 1, the signal to noise (S/N) ratio of fluorescence detection is proportionate to $\sqrt{S}$. Therefore, it is necessary to increase the value of S itself in order to increase the S/N ratio value. There are two means for increasing the value of S. One is to increase the intensity of photon being irradiated. And the other is to increase the efficiency of fluorescence collection. Any irradiation of light excessively strong risks to destroy the fluorescent substance labeling the biological specimen, and therefore there is a limit to this method. Accordingly, the efficiency of fluorescence collection of the detection system must be increased to the maximum extent possible. In other words, the numerical aperture (NA) of the detection system must be increased to the maximum extent possible. In order to detect the fluorescence from one molecule with a good S/N ratio, a NA larger than one is preferable. However, in order to achieve NA>1 by using a sample cell 2 having a generally flat bottom, the lens 5 must be immersed in a liquid as described in JP-A No. 85443/2004. In other words, the space between the lens 5 and the sample cell 2 must be filled with a liquid. As the liquid-immersion system involves a step of filling the space between the lens and the sample cell with a liquid, its operability is somewhat lower than that of the dry system. In case of analyzing a variety of samples while moving the sample cell, the troublesomeness of operation is remarkable. And this leads to a high risk of generating bubbles in the liquid with which the cell is filled and of impeding the transmission of fluorescence. Although there are systems wherein the process of charging liquid or removing bubbles is automatized as shown in JP-A No. 85443/2004, a rise in the cost of equipment is unavoidable, and the troublesomeness of filling liquid and replacing sample cells remains.

Although in some documents the focusing point in the sample and the conjugate point are called "focal point," this is an imprecise expression, and in the present specification we used the term "focal point" only in the sense of "a point where parallel pencils introduced to the lens from the sample side are focused in the side opposite the sample side." In order to clarify this point, in FIG. 1, we indicated fluorescence of virtual parallel pencils 4' and focal point 8. Thus, according to the prior art, the focal point 8 is not located in the pinhole.

As shown in the prior art, it is possible to realize NA>1 even in a non-liquid immersion system (dry system) by creating a curved surface on the bottom of the sample cell. When this is combined with a detection system with a pinhole as shown in FIG. 1, a system shown in FIG. 2 can be created. Since the light coming out of the sample cell shown in the prior art is divergent light, the pinhole of the pinhole plate 6 is not located at the focusing point 8 of the lens 5 also in the system of FIG. 2. According to this system, it is possible to realize NA>1 in a dry system.

SUMMARY OF THE INVENTION

Figure 2:
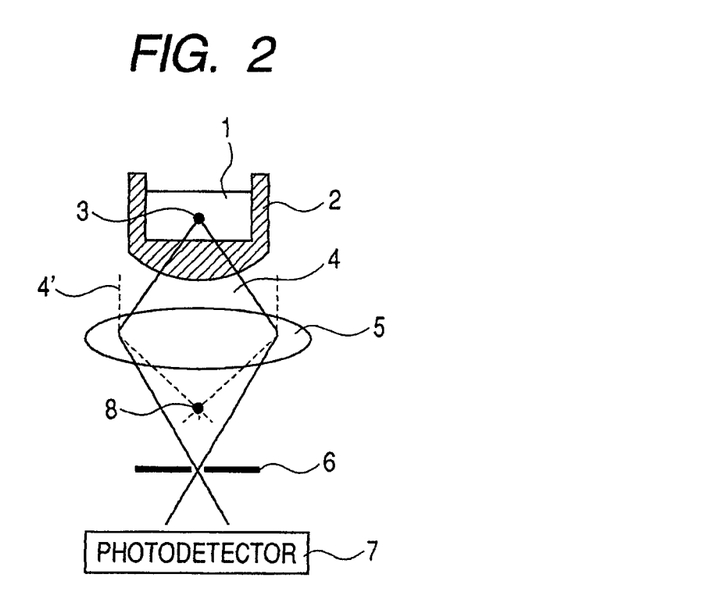
FIG. 2 is an illustration of the structure combining a sample cell whose bottom is a curved surface and a conventional fluorescence detection system having a pinhole.
Figure 3:
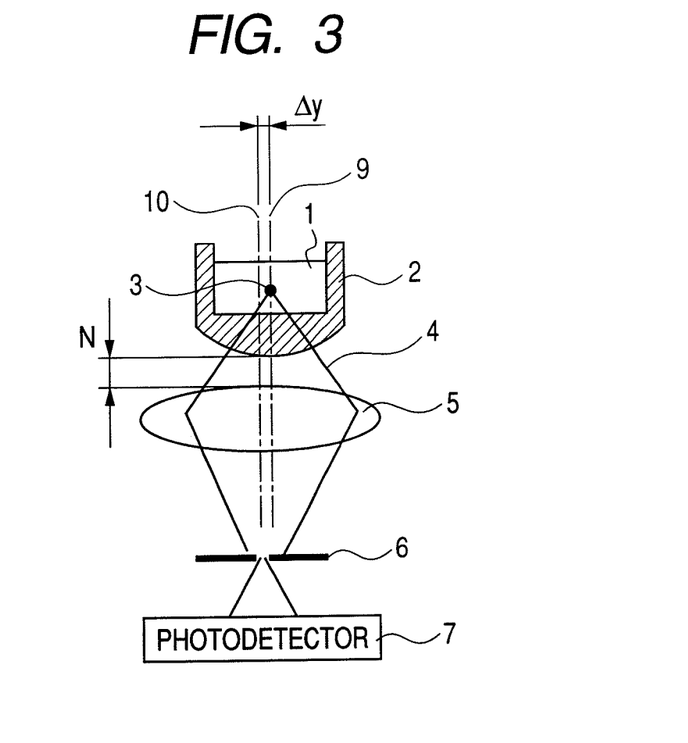
FIG. 3 is an illustration of the case wherein the relative position of the sample cell and the collection lens has shifted one against the other in the conventional optical system.

In the system shown in FIG. 2, the divergent light passing through the sample cell 2 is detected and unless the central axis of the sample cell 2 and the optical axis of the collection lens 5 agree very precisely and the distance between the sample cell 2 and the collection lens 5 agrees very precisely to a predetermined value, an aberration occurs, and the image on the pinhole at the focusing point 3 becomes blurred. As a result, the efficiency of detecting fluorescence falls down and at the same time the efficiency of removing the background light by the pinhole falls down, resulting in a decline of the S/N ratio. FIG. 3 shows how a displacement of the central axis 9 of the sample cell 2 from the optical axis 10 of the collection lens 5 resulted in a blurred image at the focusing point 3. Although it is difficult to express in the figure, a shift in the relative positions of the sample cell 2 and the collection lens 5 in the direction of the optical axis produces a similar effect. Therefore, in a system as the one shown in FIG. 2, it is necessary to control very precisely the relative positions of the sample cell 2 and the collection lens 5. This not only results in a higher cost, but as the sample cell 2 is an item that must be replaced frequently, it is not practical to proceed to a precise positioning every time the sample cell 2 is replaced.

Thus, in order to obtain a degree of brightness of NA>1 using the prior fluorescence detection system with a pinhole, it is necessary either to fill the space between the collection lens and the sample cell with a liquid or to position the sample cell very precisely in relation to the lens. Both of these approaches are not suitable for automated processing of a large number of samples.

In the present invention, a sample cell the outer surface of the bottom of which is curved acting as a lens is used. Excitation beams are irradiated from the bottom of the sample cell as collimated beams and the beams focused at the focusing point in the sample solution. The fluorescence generated by the irradiation of the excitation beams are taken up as the collimated beams from the bottom of the sample cell, are collected by the collection lens, and are detected by the photodetector. At this time, the position of the pinhole is adjusted to agree with the focusing point of the collection lens, and a pinhole plate is installed between the sample cell and the photodetector. Or, in stead of using a pinhole plate, the photodetector is located at such a position where the photosensitive area of the photodetector agrees with the focusing point of the collection lens.

According to the present invention, NA>1 can be realized in a dry system, and the effect of removing the background light can be obtained without a high-precision positioning of the sample cell.

DESCRIPTION OF THE PREFERRED EMBODIMENTS

Figure 4:
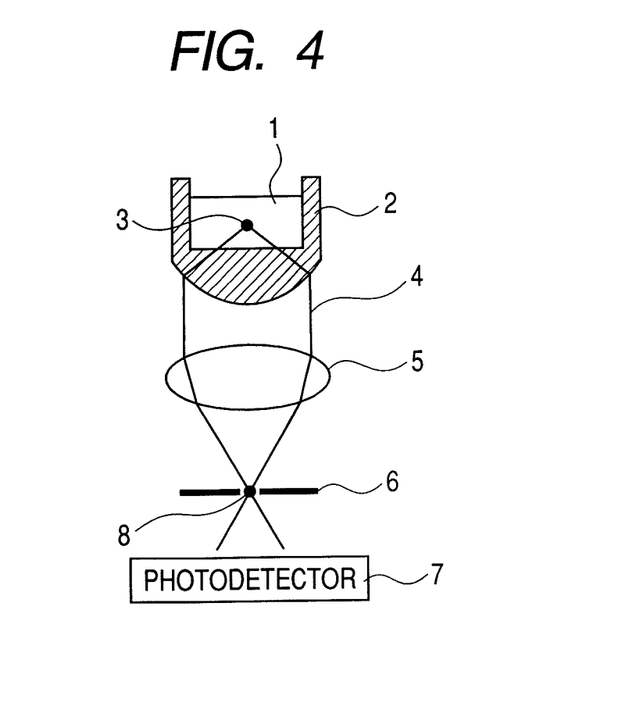
FIG. 4 is an illustration of the structure of a detection optical system according to the present invention.

FIG. 4 is an illustration showing the structure of the detection system unit of the apparatus for photon detection according to the present invention. In the present invention, as shown in FIG. 4, the bottom of the sample cell is curved so that the fluorescence emitted from the focusing point 3 may constitute parallel pencils when they are irradiated from the sample cell, and the pinhole is created at the focusing point 8 of the fluorescence collection lens 5.

Figure 5:
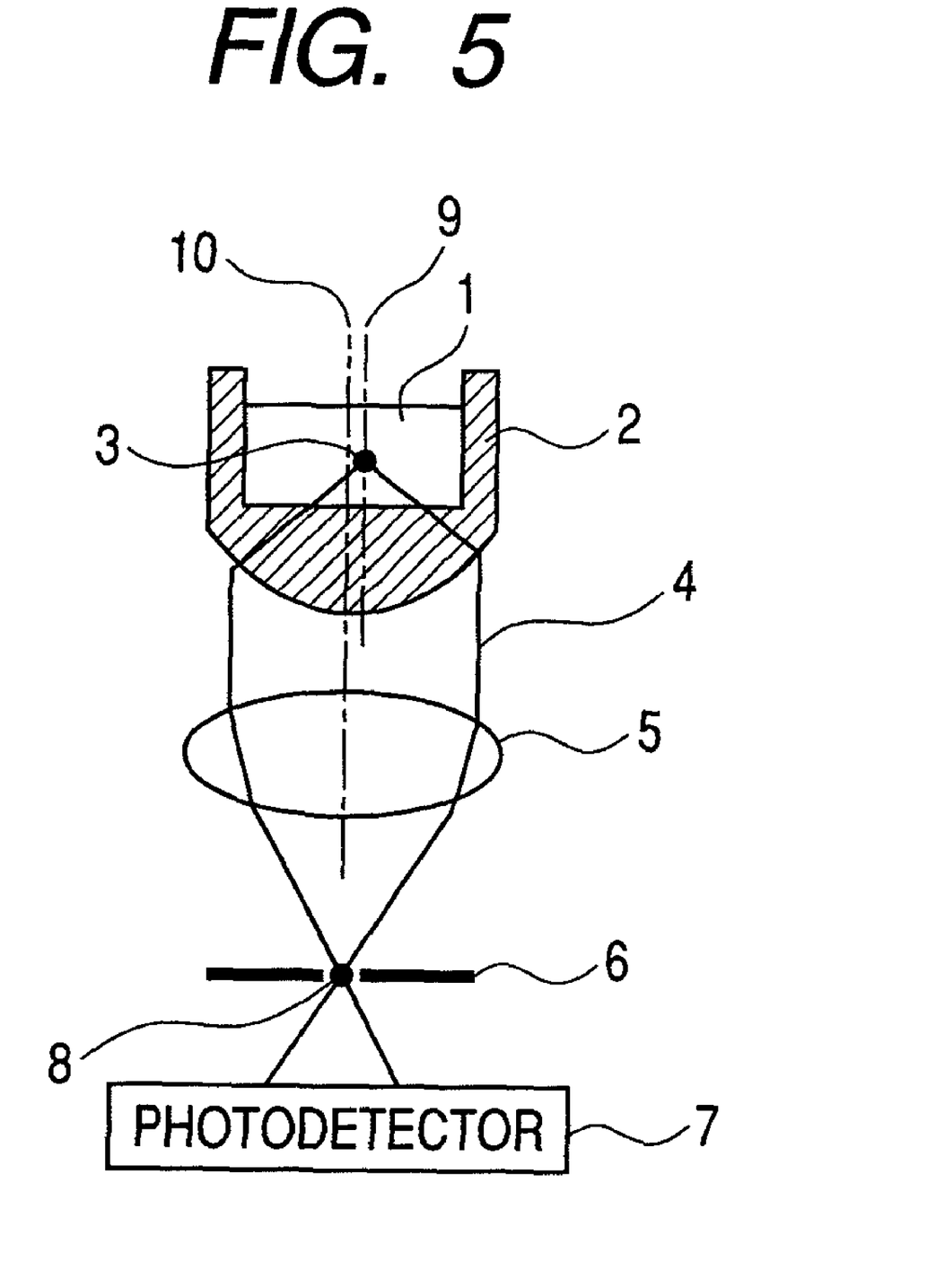
FIG. 5 is an illustration of the case wherein the relative position of the sample cell and the collection lens has shifted one against the other in the detection system according to the present invention.

FIG. 5 is a schematic illustration of the detection system shown in FIG. 4 in which the relative positions of the sample cell and the collection lens have shifted in the vertical direction of the optical axis from the best positions. As a result of thus creating parallel pencils between the sample cell and the collection lens, no aberration occurs even in case of a displacement of both of them, and a high ratio of fluorescence passing through the pinhole is maintained.

The representative materials of the member through which photons are allowed to transmit are quartz, BK7, and acrylic plastic, and the refractive index of these materials is approximately 1.5 (to be more precise 1.46-1.54). The lens for optical disks and the like are constituted by the materials mentioned above. On the other hand, as the inner side of the sample cell according to the present invention is in contact with a liquid having a refractive index of 1.3-1.4, it is expected that, in view of the refractive index of 1.5, the refractive power of the inner surface would be insufficient. Accordingly, we carried out a thorough analysis on the refractive index of the materials and the achievable NA based on a beam pursuit simulation. In the following description, the refractive index of the cell materials is shown by n.

Figure 6:
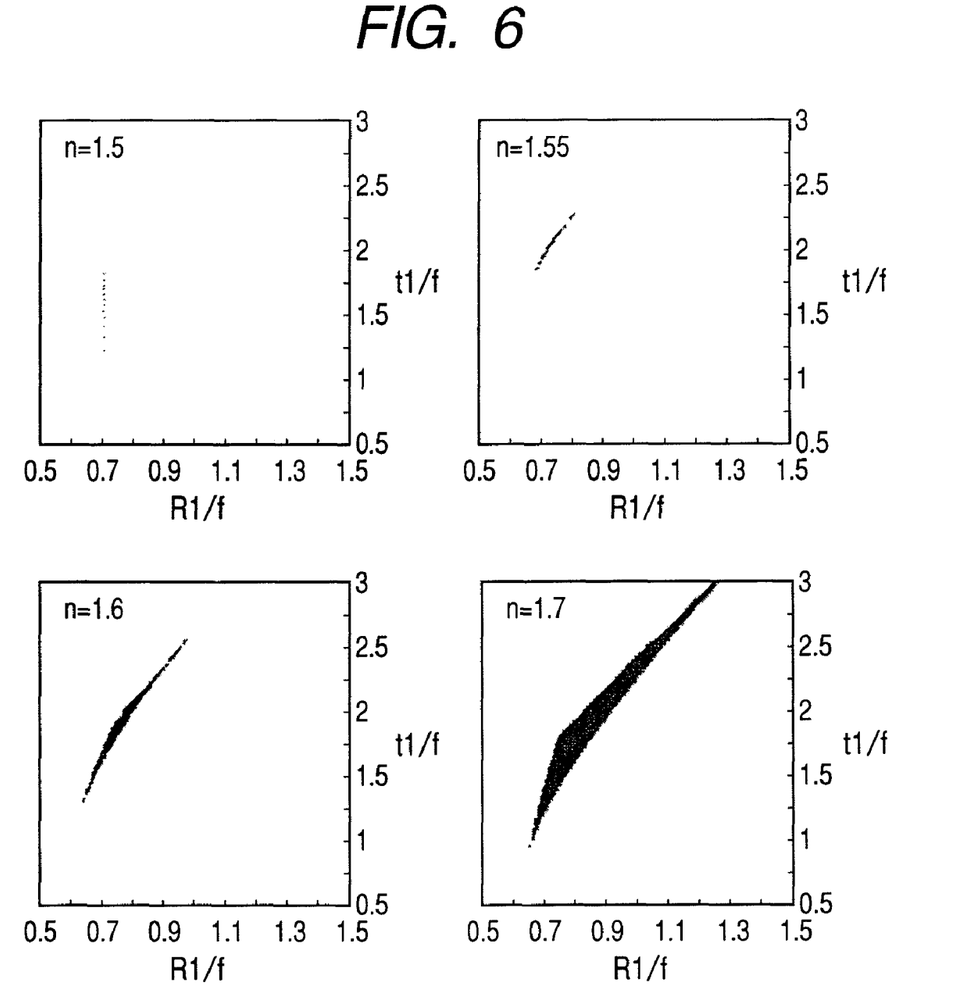
FIG. 6 represents graphs showing the range of forms of sample cell where NA is >1.

As is well known, the form of making beams from one point parallel materially without aberration is primarily determined only by three parameters: the radius of curvature R1 at the top of the outer surface, the focal distance f when the sample cell is considered as a type of lens system, and the thickness t1 on the central axis. When similar forms are considered as the identical form, independent parameters representing the form of the sample cell are limited to the standardized radius of curvature (R1/f) and the standardized thickness (t1/f). In other words, the form of the sample cell is represented by the combination of these two values (R1/f, t1/f). And when the angle θ formed by the tangential plane of the outer surface of the sample cell and the plane orthogonal with the central axis of the cell becomes larger than the Brewster's angle arctan (n), the reflectance of fluorescence on the outer surface of the cell increases sharply, and the beams cease to transmit effectively. Accordingly, we calculated by a simulation the range of the form of the cell by which NA will be >1 while meeting with the requirement of θ<arctan(n). The result obtained is shown in FIG. 6. The range painted completely in black is the range where NA is >1. Thus, as long as n=1.5, there is no range where NA is >1, and n must be at least n≧1.55 to obtain NA>1, and it is preferable that n≧1.6 to obtain NA>1 in a wider range. Therefore, a refractive index of 1.55 or more is required as the requirement for the material of the sample cell according to the present invention. And preferably the refractive index should be 1.6 or more, and more preferably the same should be 1.7 or more.

The apparatus for photon detection according to the present invention can be used as a low-cost and convenient fluorescence correlation spectrometer, a high-sensitivity fluorescence plate reader, a flow site meter and the like.

We will describe below specifically the embodiments of the present invention with reference to drawings.

First Embodiment

Figure 7:
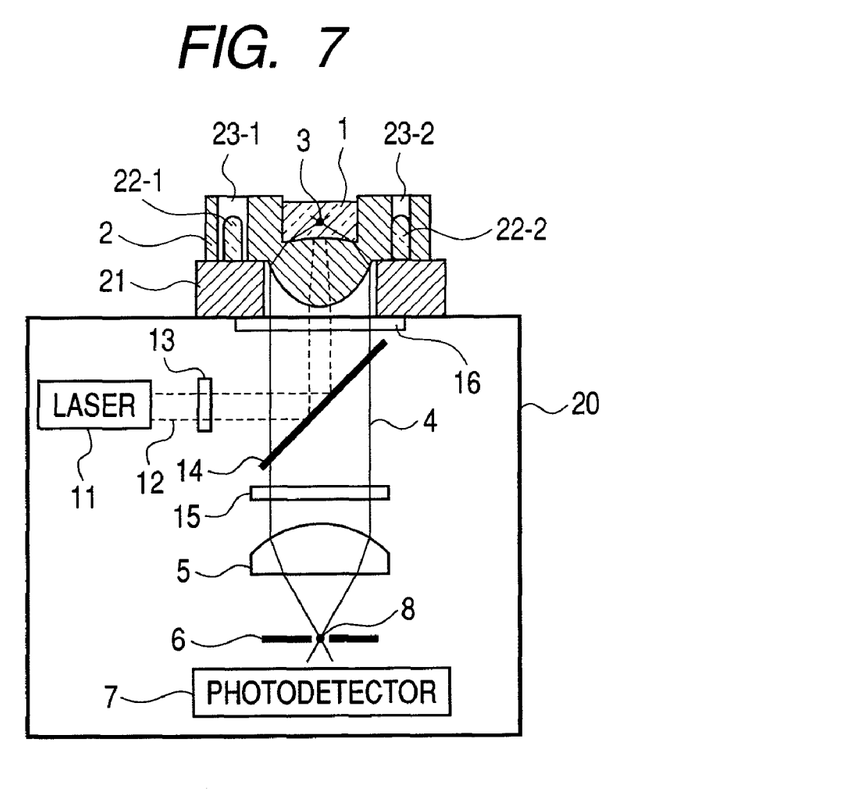
FIG. 7 is an illustration of the structure of the first embodiment of the present invention.

FIG. 7 is an illustration of the structure of the first embodiment of the apparatus for photo detection according to the present invention. The light source 11 is a laser with a wavelength of 532 nm, and an output of 1 mW. The parallel excitation beams 12 emitted by the light source 11, after having enhanced their spectrum purity while passing through an excitation filter 13, are reflected by a dichroic mirror 14, are irradiated onto the bottom of the sample cell 2 as they remain parallel pencils to be focused at the focusing point 3 in the sample 1. The fluorescence 4 emitted from the biomolecules existing at the focusing point 3 by the irradiation of the excitation beams is emitted from the bottom of the cell 2 as parallel pencils due to the refraction at the boundary surface of the cell, transmits the dichroic mirror 14, shields the components having wavelength other than the fluorescence wavelength such as the scattered light of the excitation beams of 523 nm with a fluorescence filter 15, and is focused into the pinhole created on the pinhole plate 6 by the collection lens 5. The pinhole is located at the position of the focal point 8 of the collection lens 5. The pinhole shields the luminescence from parts other than the focusing point in the sample and the sample cell, and only the fluorescence from the focusing point passes through the pinhole and is detected by the photodetector 7. The NA of this detection system is 1.15, the diameter of the excitation beam at the focusing point is 1 μm, the image magnification of the collection lens 5 is 10 times, and the diameter of the pinhole is 10 μm. The solvent of the sample is SSC buffer with a refractive index of 1.351. The material of the sample cell is resin with a refractive index of 1.7. The space between the sample cell and the collection lens is occupied by air, and the creation of a curved surface on the bottom of the collection lens thus enabled us to realize a NA larger than 1 in the dry system.

The outer surface and the inner surface of the sample cell 2 are respectively aspheric as shown by the following equation.

$$z = \frac{cr^2}{1+\sqrt{1-(1+K)c^2r^2}} + Ar^4 + Br^6 + Cr^8 + Dr^{10} + Er^{12} + Fr^{14} + Gr^{16} + Hr^{18}$$ [Equation 1]

In this equation, $r=\sqrt{(x^2+y^2)}$, c is the curvature at the top, K is the conic constant, and A, B, C, D, E, F, G, H are aspheric coefficients The conic constant and the aspheric coefficient representing the outer surface and the inner surface of the sample cell 2 in the present embodiment and the thickness in the central axis are shown in Table 1. The unit of r and z is mm. By making both surfaces aspheric, it is possible to convert the fluorescence from the focusing point into parallel pencils with a resolution at the diffraction limit of wave aberration of 0.07 λrms or less. The NA for detection obtained by the present embodiment is 1.15.

TABLE 1

| | Outer surface (air side) | Inner surface (sample solution side) |
|---|---|---|
| Refractive index | 1.7 | 1.351 (Sample refractive index) |
| Thickness on the central axis | 3.88 | 0.54286 (Distance with the focusing point) |
| C | 0.506894 | 1.7370 |
| K | −3.9 | −6.49 |
| A | 0.5680637E-1 | 0.3759345 |
| B | −0.160145E-1 | −0.9478041 |
| C | 0.6405858E-2 | 1.61106 |
| D | 0.2005395E-2 | 1.805153 |
| E | 0.4605048E-3 | 1.298703 |
| F | −0.68272E-4 | −0.5743903 |
| G | 0.5808605E-5 | 0.1417377 |
| H | 0.2099961E-6 | 0.1490973E-1 |

The light source 11, the photodetector 7 and optics for transmitting or reflecting beams are fixed inside the structure 20. A hole is perforated in the structure 20 to allow the passage of beams between the sample cell 2 and the dichroic mirror 14, and this hole is covered with a transparent window plate 16. The fixation of this window plate has the effect of preventing samples flowing out of the sample cell and dusts contained in the atmosphere from sticking on the optics below the dichroic mirror.

Figure 8:
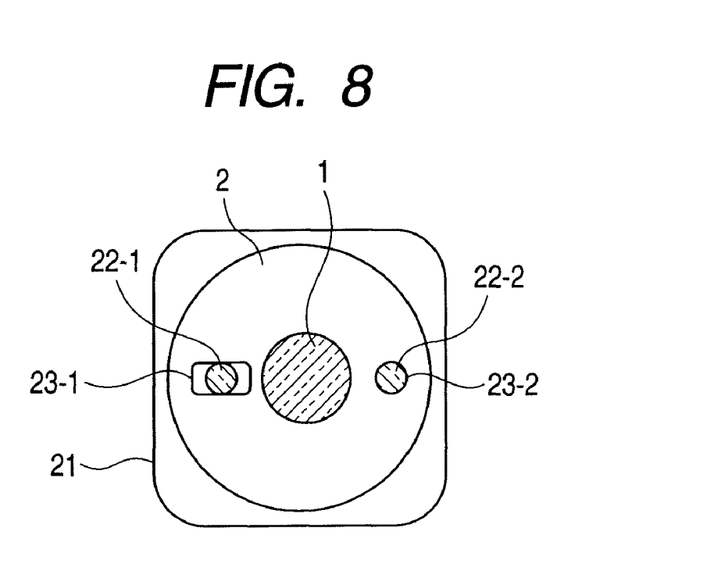
FIG. 8 is an enlargement of the top plan view of the portion above the cell stand 21.

The sample cell 2 is set on the cell table 21 fixed on the structure 20. And the sample cell 2 is perforated to create positioning holes 23-1 and 23-2. By placing the sample cell 2 in such a way that positioning pins 22-1 and 22-2 fixed on the cell table 21 may fit in these positioning holes, the sample cell 2 is automatically positioned in such a way that the distance between the optical axis of the fluorescence 4 and the excitation beams 12 and the symmetry axis of the sample cell may be limited to 0.1 mm or less. FIG. 8 is a top plan view of the section above the cell table 21. Thus, the positioning holes 23-1 and 23-2 of the sample cell 2 are fitted respectively with the positioning pins 22-1 and 22-2.

Figure 9:
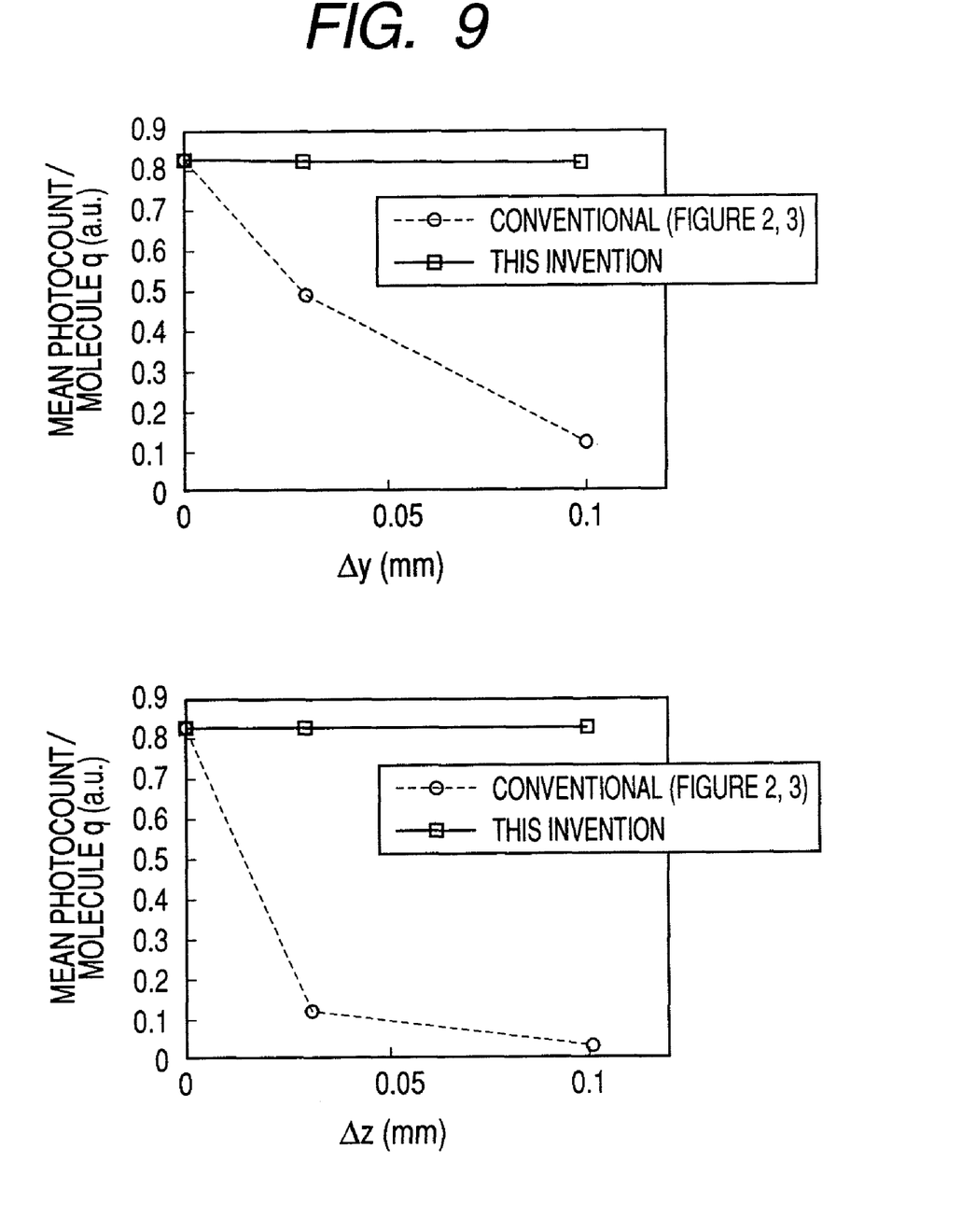
FIG. 9 represents graphs showing the relationship between the efficiency of fluorescence detection and the displacement of the relative position of the collection lens and the sample cell in the system of the present invention and the system shown in FIG. 2.

FIG. 9 represents graphs showing the relationship between the divergence of the cell position from the reference position in the present embodiment and in the system resulting from the replacement of the detection system of the present embodiment by the conventional detection system shown in FIG. 2 and the efficiency of detecting fluorescence from biomolecules. In this case, both the inner surface and the outer surface of the sample cell are spheric, and the sample cell has almost the same NA of 1.14 as the first embodiment. Δy represents a shift from the ideal position of the sample cell in the direction of crossing vertically with the optical axis of the detection system while Δz represents a shift towards the optical axis. As shown in FIG. 9, while a mere displacement of the sample cell by 10 μm in a system as the one shown in FIG. 2 leads to a sharp decline in the efficiency of detecting fluorescence, according to this invention, even if the position of the sample cell is displaced by 0.1 mm, the efficiency remains virtually unchanged.

As described above, according to the present invention, it is possible to realize NA>1 by the dry system. In addition, a system of fluorescence detection wherein the efficiency of detection does not practically fall down even if the position of the sample cell is displaced. As a result, in the case of analyzing a large number of samples by replacing sample cells, it will be no longer necessary to adjust the position of fixing the sample cells, and this will be very advantageous in practical use. And as the precision of positioning sample cells is not severe, it will be possible to continually analyze automatically a large number of samples by driving plates carrying a large number of sample cells by automatic parallel advancing stages. In particular, in the case of driving plates at a constant speed, the time of moving over a width of ±0.1 mm or more can be used for measurement according to the present invention, while nothing other than the time required for moving over a width of approximately 0.01 µm can be used for measuring a sample according to the system shown in FIG. 2. In other words, more than ten times the measuring time can be taken and an improvement of S/N ratio of √10-3 or more can be expected.

Second Embodiment

Figure 10:
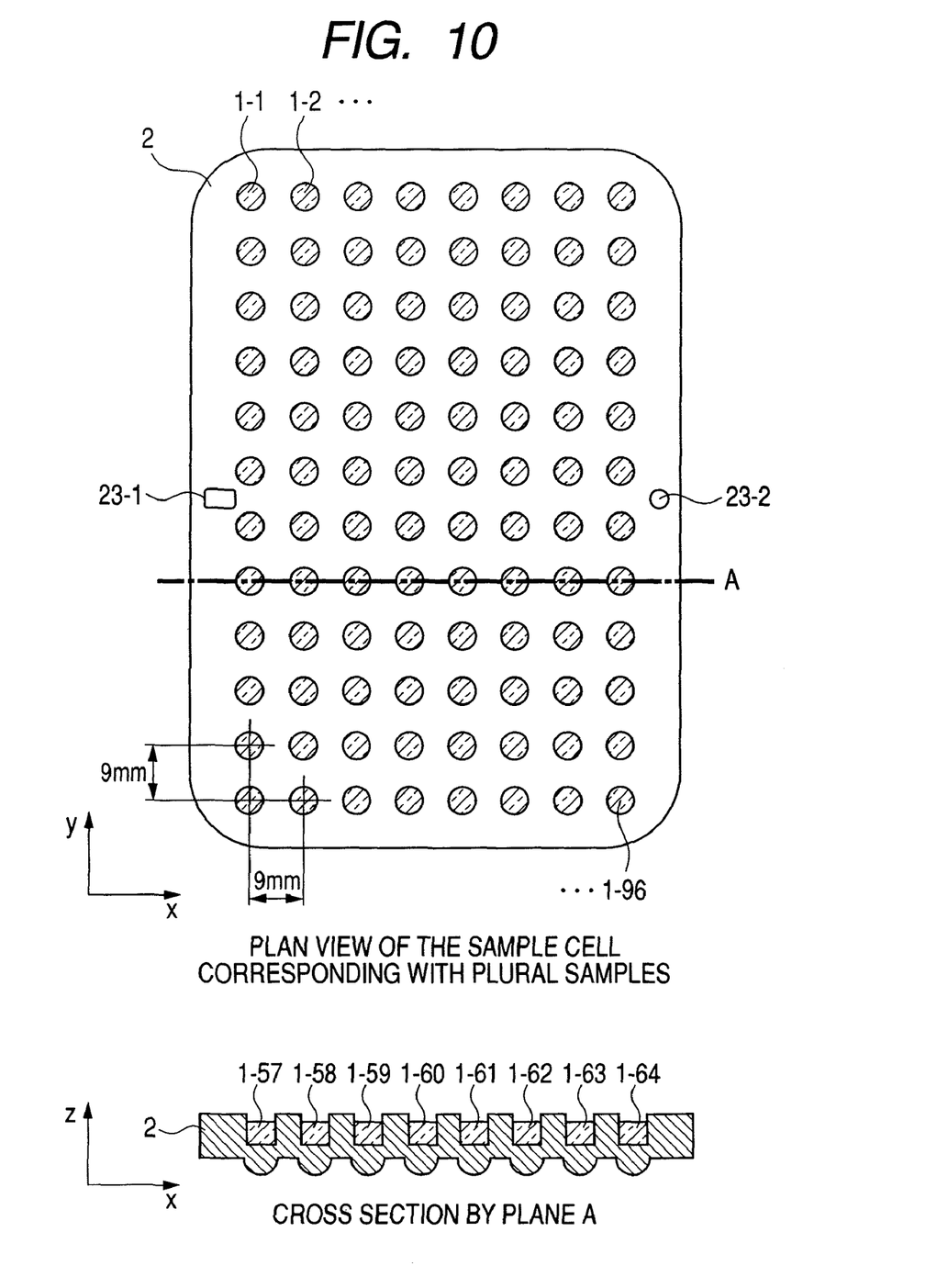
FIG. 10 is the front view and the sectional view of the cell according to the second embodiment of the present invention.

FIG. 10 represents a top plan view and cross sectional view of the sample cell according to the second embodiment of the present invention. According to the present embodiment, we created a plurality of wells on the sample cell 2 so that a plurality of samples 1-1 . . . 1-96 may be introduced therein, and we formed the bottom of each well to constitute a curved surface so that the similar effect as the first embodiment may be obtained from the same. In the present embodiment, we disposed the wells at the 9 mm pitch identical to the sample preparing plate generally used arranged in 8 rows and 12 lines of wells per plate so that samples may be transported easily by the sample dispensing robot available on the market. Of course, a 4.5 mm pitch for 16 rows and 24 lines of wells per plate can be adopted. Like in the first embodiment, we created two positioning holes 23-1 and 23-2 in each sample cell 2.

Figure 11:
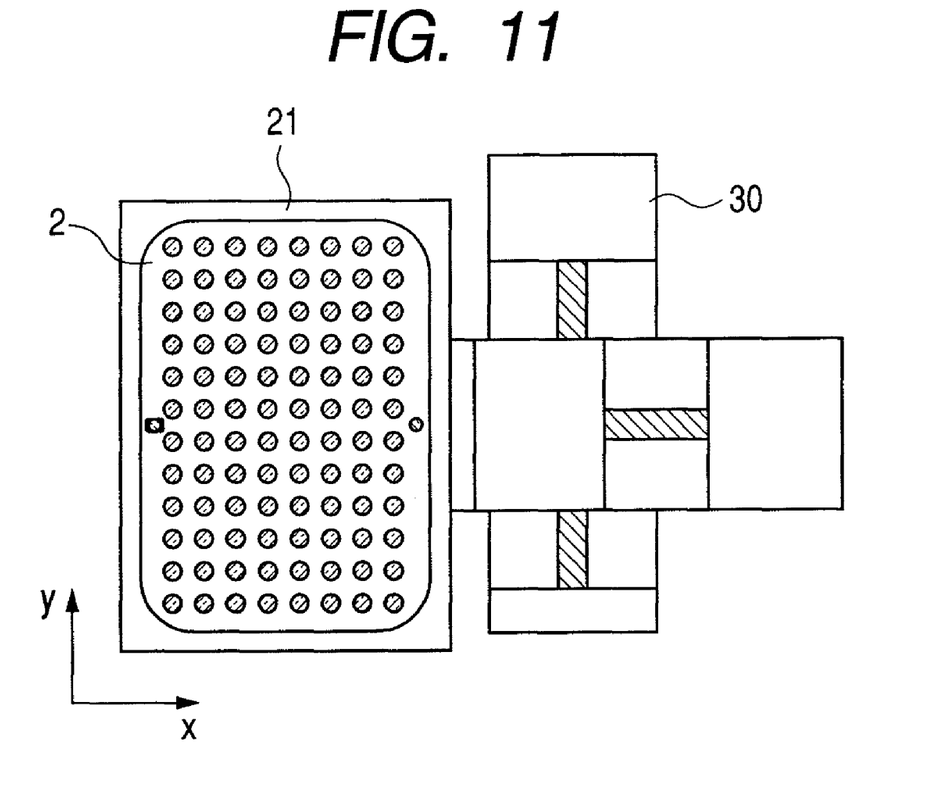
FIG. 11 is the front view of the vicinity around the cell according to the second embodiment of the present invention.

The optical system of irradiating excitation beams and detecting fluorescence in the present embodiment is basically same as the first embodiment. FIG. 11 is an enlargement of the periphery around a sample cell 2 fixed on an apparatus for photon detection. In the present embodiment, the table 21 for accommodating a sample cell 2 is fixed on an automatic xy stage 30, and the sample cell 2 is carried in the x and y directions. The precision of positioning of the automatic xy stage 30 is ±0.05 µm, and the sample cell 2 is positioned and stands still so that the central axis of each well may agree with the optical axis of the detection optical system to this precision, and the fluorescence from these well is detected thereby. By the computer control, the cycle of this positioning and detection of fluorescence is repeated automatically to each sample 1-1 . . . 1-96. Thus, in the present embodiment, the action of setting once a sample cell 2 on the table 21 has the effect of automatically analyzing 96 samples. Of course, if a sample cell with 16 rows and 24 lines of wells is used, 384 samples can be automatically analyzed. Needless to say, the number of rows and lines of samples is not limited to the values mentioned above.

Third Embodiment

The third embodiment of the present invention is constituted almost in the same way as the second embodiment. However, the xy stage 30 is not brought to a standstill every time when the axis of each well and the optical axis of the detection system of fluorescence agree, and is driven at almost at a fixed speed over a row, and fluorescence is detected while the axis of the well and the optical axis of the detection system agree within a range of ±0.1 mm. With the conventional optical system, fluorescence could be detected efficiently only while both axes agreed within a range of ±0.01 mm. However, according to the optical system of the present invention as shown in FIG. 9, fluorescence can be detected efficiently while both axes agree within a range of ±0.1 mm. As a result, it has become possible to detect fluorescence during a length of time approximately ten times of the conventional system, and it will be possible to detect fluorescence with a sufficient S/N ratio even by such a continuous constant speed driving. As it is no longer necessary to position the sample cell 2 with a high precision according to the present embodiment, no stepping motor is required as the motor for driving the automatic xy stage, and as low-priced DC motor can be used to cope with the situation, it will be possible to obtain the cost reducing effect as a result.

Fourth Embodiment

Figure 12:
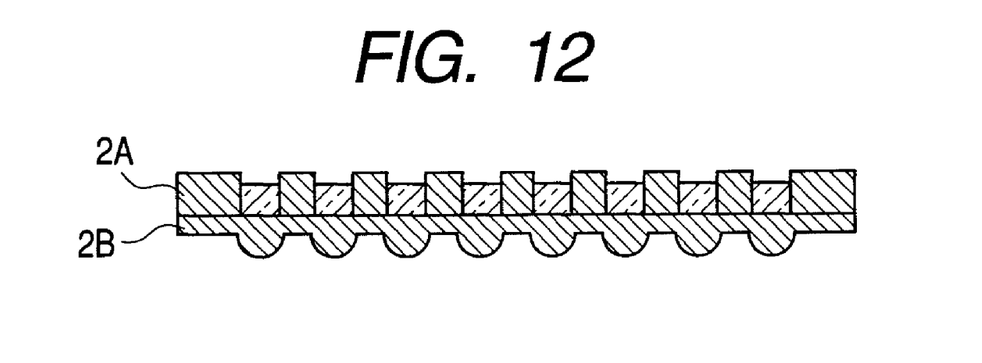
FIG. 12 is the sectional view of the cell according to the fourth embodiment of the present invention.
Figure 13:
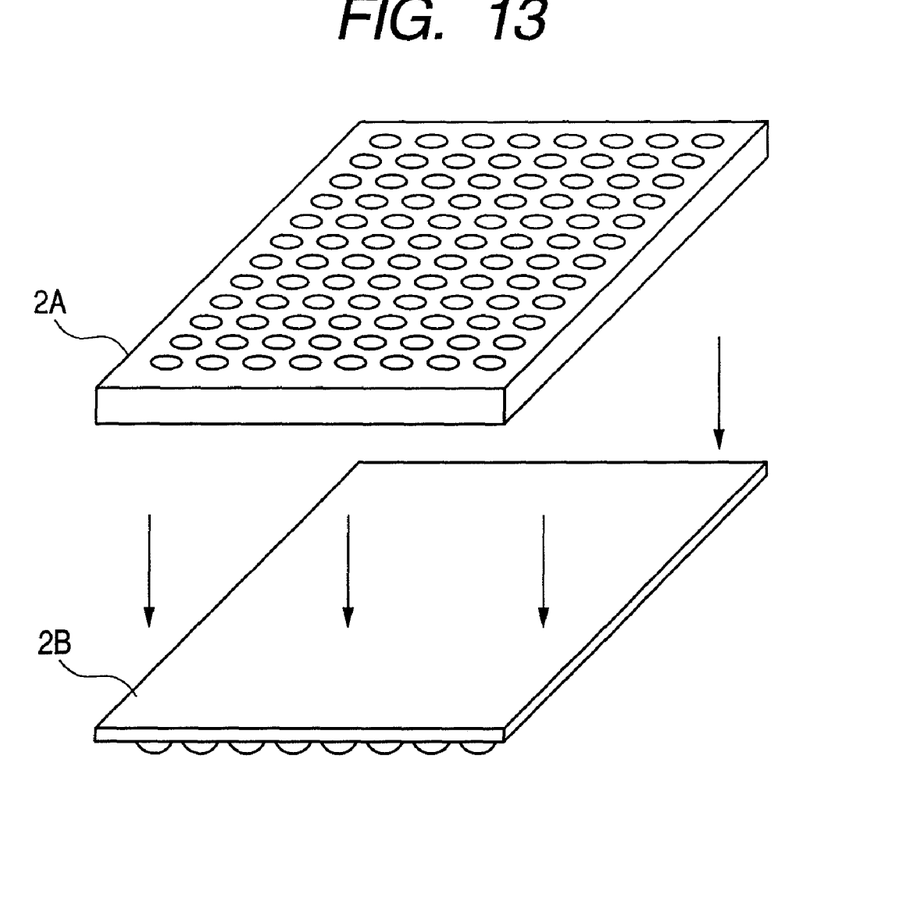
FIG. 13 is an illustration describing the fabrication process of the cell according to the fourth embodiment of the present invention.

FIG. 12 is a sectional view of a sample cell 2 according to the fourth embodiment of the present invention. The form of the sample cell 2 according to the present embodiment is almost the same as the second embodiment. However, while the sample cell according to the second embodiment was an integrally formed plastic resin structure 2, the sample cell according to the present embodiment is formed by gluing together two different members 2A and 2B. FIG. 13 is an illustration showing the fabrication process of the sample cell according to the present embodiment. A member 2A wherein columnar through holes are arranged in an array is positioned and glued together by means of an adhesive with another member 2B where lenticules constituting the bottom of sample cells on the lower surface are arranged in an array in the same way as the member 2A.

As a result of fabricating the sample cells by gluing together two members in this way, the form of each member is simplified and the manufacturing cost has sharply decreased, and in spite of the addition of a gluing process, we obtained the effect of a reduction in the total manufacturing cost. Particularly the member 2A being simply a flat substrate with through holes created therein is not only easy to fabricate and unlike the member 2B needs not to be transparent. Therefore, the margin of selecting the material has expanded remarkably. The adoption of an opaque material for the member 2B facilitates the shielding of outside lights. We described here a sample cell having a plurality of wells. However, it is possible to fabricate a sample cell having a single container of sample as shown in FIG. 7 by gluing together two members.

Fifth Embodiment

Figure 14:
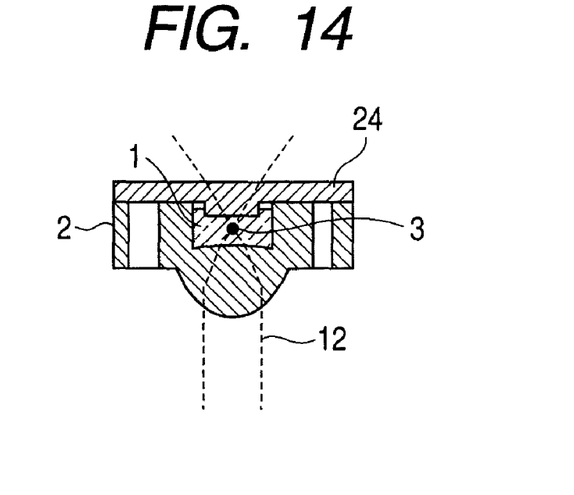
FIG. 14 is the sectional view of the vicinity around the cell according to the fifth embodiment of the present invention.

FIG. 14 is an enlargement of the sectional view of the vicinity of the sample cell 2 according to the fifth embodiment of the present invention. According to the present embodiment, the sample cell 2 has a transparent cover 24, and a part of the lower surface of the cover 24 is designed to come into contact with the surface of the sample solution. As a result, the excitation beams transmit upward through the sample cell without scattering at the sample/air interface, and reduce the rise of the background light caused by the scattered light at the surface of sample. As the material of the cover 24, materials whose refractive index is close to the sample can be preferably used. As the refractive index of the material according to the present embodiment was 1.36, we used an acrylic resin with a low refractive index (refractive index: 1.42). In addition, it is possible to reduce further scattering by creating an anti-reflection coat on the upper surface (air/cover interface) of the cover 24.

Sixth Embodiment

Figure 15:
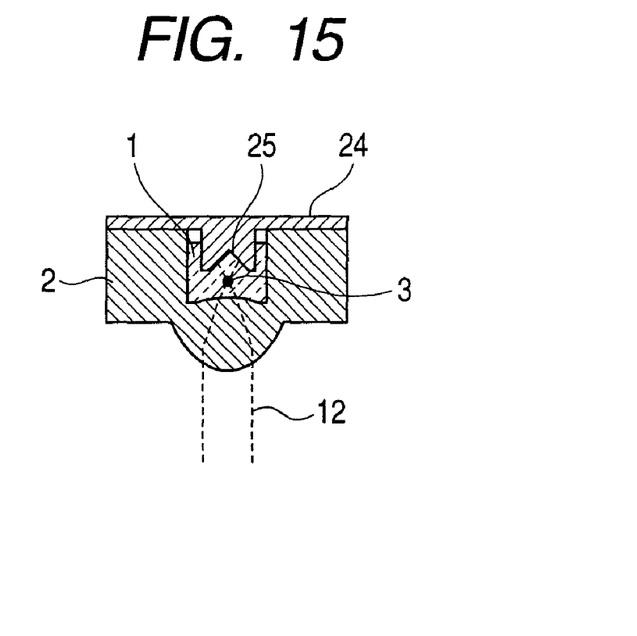
FIG. 15 is the sectional view of the vicinity around the cell according to the sixth embodiment of the present invention.

FIG. 15 is an enlargement of the sectional view of the vicinity of the sample cell 2 according to the sixth embodiment of the present invention. In the present embodiment, we created a cover 24 on the sample cell 2 like the fifth embodiment. However, we obtained the same effect as the fifth embodiment by adopting a light-absorbing material instead of a transparent member. In the present embodiment, we used a black polycarbonate as the material of the cover 24. However, any material that absorbs light well may do. We tried to improve the efficiency of absorption of light by creating a conic depression 25 at a point where the light from the cover 24 is irradiated, Even if the material of the cover itself does not absorb light, it is possible to obtain the same effect by applying a light-absorbing coating on the area irradiated by the excitation beam.

Seventh Embodiment

Figure 16:
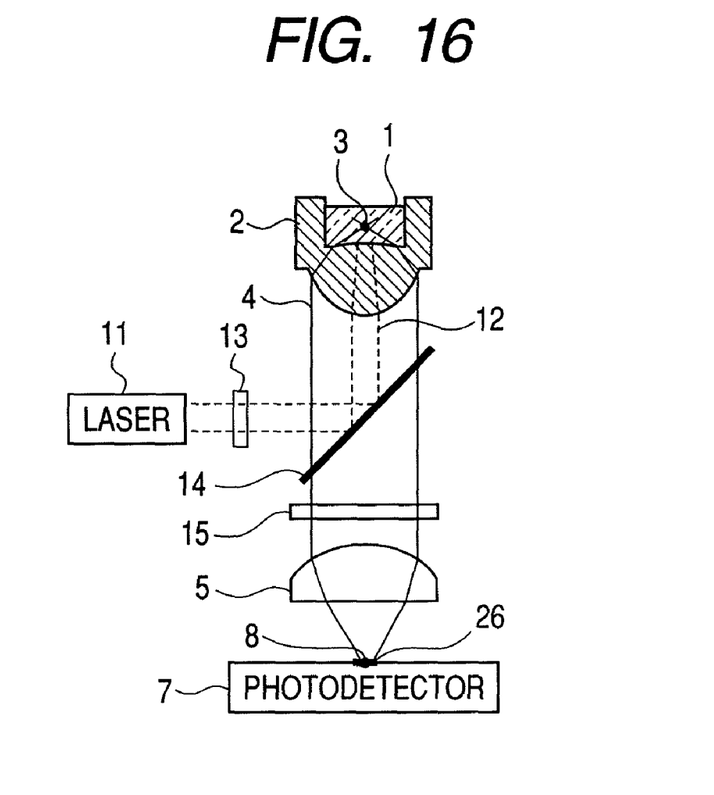
FIG. 16 is an illustration of the structure of the seventh embodiment of the present invention.

FIG. 16 is an illustration showing the optical system of the seventh embodiment of the present invention. We constituted the present embodiment basically in the same way as the first embodiment. However, we omitted the mechanical pinhole plate 6 by arranging the photosensitive area 26 of the photodetector 7 in such a way that the focusing point 8 of the collection lens 5 may be contained therein. According to this structure, it is possible to obtain the same effect of removing the background light as disposing a gobo having a hole of a diameter equal to the effective diameter of the photosensitive area at the focusing position without pinhole. The peculiar effect of this structure is the possibility of reducing a component part of the structure.

It is possible to apply respectively the structures described in the embodiments 1-6 described above to the apparatus for photon detection having the optical system of the present embodiment.

What is claimed is:

1. An apparatus for photon detection comprising:
   a sample cell having a top and a bottom, said bottom having an inner surface an outer surface, and said bottom having a refractive index for converting divergent light inside of said sample cell into collimated light irradiated from said outer surface of said bottom of said sample cell, wherein said inner surface of said bottom of said sample cell is aspheric and rotationally symmetric;
   a photodetector for detecting said collimated light irradiated from said bottom of said sample cell;
   a pinhole plate located between said sample cell and said photodetector; and
   a collection lens located between said sample cell and said pinhole plate;
   wherein said pinhole plate is fixed in such a way that a position of a pinhole created on said pinhole plate coincides with a focus of said collection lens.

2. The apparatus for photon detection according to claim 1, further comprising a light irradiating unit for irradiating said bottom of said sample cell with substantially collimated excitation beams.

3. The apparatus for photon detection according to claim 2, wherein a sample solution is held in said sample cell, and said exciting beams are focused in a pinpoint in a sample solution contained in said sample cell.

4. The apparatus for photon detection according to claim 2, wherein a dichroic mirror is located between said sample cell and said collection lens, and said light irradiating unit irradiates a sample solution contained in said sample cell with excitation beams through said dichroic mirror.

5. The apparatus for photon detection according to claim 2, further comprising:
   a cell table on where said sample cell is set;
   a positioning hole provided in said sample cell; and
   a positioning pin fixed on said cell table;
   wherein said sample cell is set on said cell table such that said positioning pin is fit in said positioning hole, and a distance between an optical axis of said substantially collimated excitation beams and a symmetry axis of said sample cell are substantially matched.

6. The apparatus for photon detection according to claim 1, wherein a transparent partition is provided between said sample cell and said collection lens.

7. The apparatus for photon detection according to claim 1, wherein an outer surface of said bottom of said sample cell is curved. cell and said collection lens.

8. The apparatus for photon detection according to claim 7, wherein said outer surface of said bottom of said sample cell is aspheric.

9. The apparatus for photon detection according to claim 1, wherein said top of said sample cell has a cover made of a transparent or partially light-absorbing material, and at least a part of a lower side of said cover is in contact with a sample solution contained in said sample cell.

10. The apparatus for photon detection according to claim 9, wherein said cover comprises partially light-absorbing material, and said cover has a conic depression at a point where said cover is irradiated.

11. The apparatus for photon detection according to claim 1,
   wherein said sample cell has a plurality of wells, each well independently containing a respective sample solution, and
   wherein said sample cell has a driving unit for driving said sample cell two- dimensionally with reference to said apparatus for photon detection.

12. The apparatus for photon detection according to claim 1, wherein a numerical aperture (NA) is greater than one (NA>1) in a non-liquid immersion system.

13. The apparatus for photon detection according to claim 1, the refractive index having a value equal to or larger than 1.55.

14. The apparatus for photon detection according to claim 1, the refractive index having a value equal to or larger than 1.6.

15. The apparatus for photon detection according to claim 1, the refractive index having a value equal to or larger than 1.7.

16. The apparatus for photon detection according to claim 1, wherein said inner surface of said bottom of said sample cell is rotationally symmetric around an axis corresponding to said collimated light.

17. The apparatus for photon detection according to claim 1, wherein said top of said sample cell has a concave opening.

* * * * *